United States Patent
Quarles

(10) Patent No.: US 11,103,444 B1
(45) Date of Patent: Aug. 31, 2021

(54) TEETH CLEANING FOR ANIMALS

(71) Applicant: B&R Plastics, Inc., Denver, CO (US)

(72) Inventor: James M Quarles, Aurora, CO (US)

(73) Assignee: B&R PLASTICS, INC., Denver, CO (US)

( * ) Notice: Subject to any disclaimer, the term of this patent is extended or adjusted under 35 U.S.C. 154(b) by 0 days.

(21) Appl. No.: 16/164,504

(22) Filed: Oct. 18, 2018

Related U.S. Application Data

(60) Provisional application No. 62/575,072, filed on Oct. 20, 2017.

(51) Int. Cl.
| | |
|---|---|
| *A61K 39/07* | (2006.01) |
| *A61K 35/742* | (2015.01) |
| *A61K 8/99* | (2017.01) |
| *A61K 8/66* | (2006.01) |
| *A23L 33/135* | (2016.01) |
| *A23K 10/18* | (2016.01) |
| *A61Q 11/00* | (2006.01) |

(52) U.S. Cl.
CPC ................. *A61K 8/99* (2013.01); *A23K 10/18* (2016.05); *A23L 33/135* (2016.08); *A61K 8/66* (2013.01); *A61K 35/742* (2013.01); *A61K 39/07* (2013.01); *A61Q 11/00* (2013.01); *A23V 2002/00* (2013.01); *G01N 2333/956* (2013.01)

(58) Field of Classification Search
None
See application file for complete search history.

(56) References Cited

U.S. PATENT DOCUMENTS

| | | | |
|---|---|---|---|
| 4,559,307 A | 12/1985 | Hopkins | |
| 5,171,682 A | 12/1992 | Shih et al. | |
| 2007/0277257 A1 | 11/2007 | Lim et al. | |
| 2018/0296475 A1* | 10/2018 | Sandvang | ...... C12Y 301/03026 |

FOREIGN PATENT DOCUMENTS

| | | |
|---|---|---|
| EP | 0549264 A1 | 6/1993 |
| WO | 2016180928 A1 | 11/2016 |
| WO | WO 2018/206553 A1 * | 11/2018 |

OTHER PUBLICATIONS

Zhang et al. J. Microbiol. Biotechnol. 24: 1405-1412, 2014.*
Divakaran D., Chandran A,. Pratap Chandran R. "Comparative study on production of a-Amylase front Bacillus licheniformis strains." Brazilian Journal of Microbiology Oct.-Dec. 2011; 42(4):1397-1404; Published Online Dec. 1, 2011 https://www.ncbi.nlm.nih.gov/pmc/articles/PMC3768710/pdf/bjm-42-1397.pdf.
Sarker P.K., Talukadar S.A., Deb P., Sayem S.A., Mohsina K. Optimization and partial characterization of culture conditions for the production of alkaline protease from Bacillus licheniformis P003. SpringerPlus. 2013;2:506; Published Online Oct. 4, 2013 https://www.ncbi.nlm.nih.gov/pmc/articles/PMC3795880/pdf/40064_2013_Article_571.pdf.
Lin X., Lee C.G., Casale E.S., Shih J.C.H. "Purification and Characterization of a Keratinase from a Feather-Degrading Bacillus lichentformis Strain." Applied and Environmental Microbiology Oct. 1992 vol. 58 No. 10 p. 3271-3275 https://aem.asm.org/content/aem/58/10/3271.full.pdf.
Zhang J., HE Z., He K. "Purification and characterization of β-mannnase from Bacillus licheniformis for industrial use." Biotechnology Letters 22, 1375-1378 (2000) https://doi.org/10 1023/A:1005844414762.

\* cited by examiner

*Primary Examiner* — Sarvamangala Devi
(74) *Attorney, Agent, or Firm* — Cochran Freund & Young LLC; Bridget A. Cochran; William W. Cochran

(57) ABSTRACT

A composition of matter for dental plaque removal comprising at least one of a strain of the bacteria *Bacillus licheniformis* and the extracellular enzymes produced by *B. licheniformis*, and at least one of a natural and synthetic polymer, are disclosed. A method of manufacturing an animal chew or food item coated with the disclosed composition of matter, and animal chews or food items produced therefrom, are also disclosed.

4 Claims, 1 Drawing Sheet

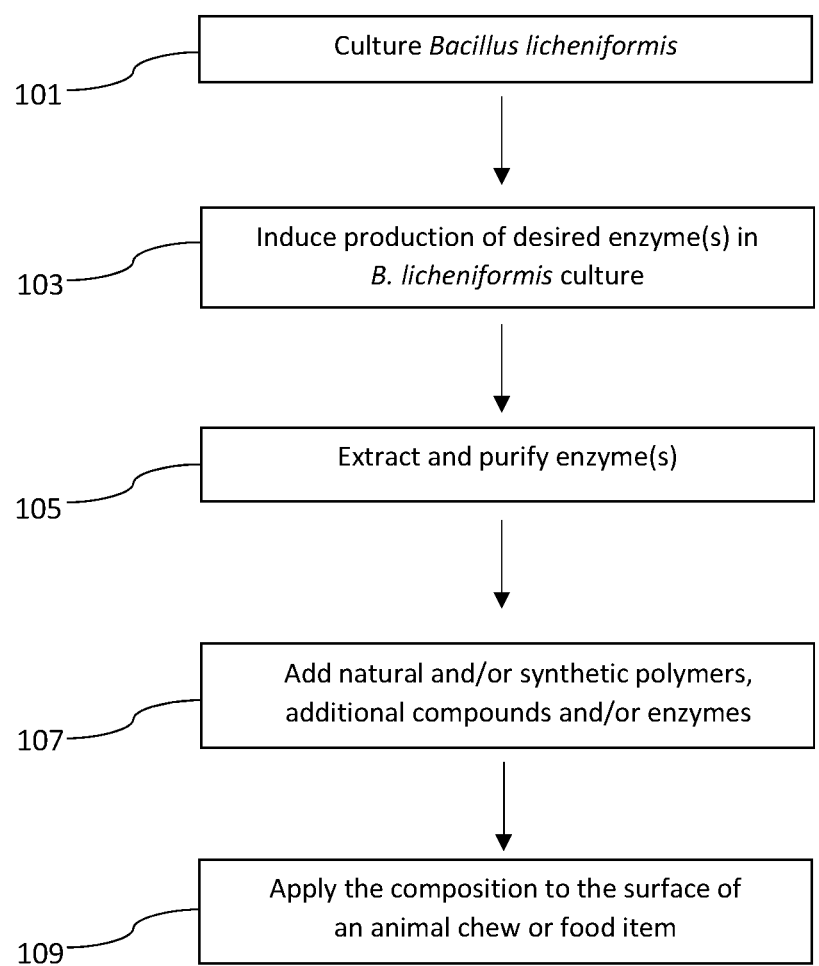

TEETH CLEANING FOR ANIMALS

BACKGROUND

*Ascophyllum nodosum* is a type of algae, commonly known as Norwegian kelp or seaweed. It is known to have many health benefits. The proteins, peptides, amino acids, fatty acids, polysaccharides, vitamins, minerals and antioxidants contained in kelp work in synergy with each other, and are believed to have anti-cancer, anti-inflammatory, anti-coagulant and hypocholesterolemic activities. Additionally, the high content of vitamins, minerals, and iodine provide added nutritional value. A variety of products for animals to chew, or gnaw on, incorporate *A. nodosum* for its nutritional and health benefits. The chewing or gnawing action provides a mechanical means to help remove dental plaque.

SUMMARY

The present disclosure has applications in the dental health sector. One embodiment discloses compositions for dental plaque removal comprising strains of the bacteria *Bacillus licheniformis*, and/or the extracellular enzymes produced by *B. licheniformis*. The compositions may further comprise natural and/or synthetic polymers or mixtures of compounds and additional bacteria, for example, strains of *Lactobacillus* to aid in the destruction of plaque.

Another embodiment discloses a composition of matter for dental plaque removal comprising at least one of a strain of the bacteria *Bacillus licheniformis* and an extracellular enzyme produced from said *B. licheniformis*, and at least one of a natural and synthetic polymer.

Another embodiment discloses a method for manufacturing an animal chew or food item comprising coating at least a portion of said animal chew or food item with a composition of matter comprising at least one of a strain of the bacteria *Bacillus licheniformis* and an extracellular enzyme produced from said *B. licheniformis*; and at least one of a natural polymer and a synthetic polymer.

In addition to the exemplary aspects and embodiments described above, further aspects and embodiments will become apparent by study of the following descriptions.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1 shows a flow diagram for a method of coating an animal chew with a composition comprising extracellular enzymes produced by *B. licheniformis*.

DETAILED DESCRIPTION OF THE EMBODIMENTS

Embodiments include methods and compositions to aid in the removal of dental plaque from animals comprising applying a composition of the bacteria *Bacillus licheniformis*, and/or the extracellular enzymes produced by *B. licheniformis* to an animal chew. The composition may further comprise natural and/or synthetic polymers or mixtures of compounds and additional bacteria, for example, strains of *Lactobacillus*. *Bacillus licheniformis*. *B. licheniformis* is an endospore forming bacteria commonly found in the soil and on bird feathers, and most recently on the seaweed *A. nodosum*, and can also be obtained from a microbial depository, for example, the American Tissue Culture Collection (ATCC) or it may also be commercially purchased, for example, from BIO-CAT Microbials. Specific enzymes produced by *B. licheniformis* may also be commercially purchased, for example, from Merck Millipore or Sigma-Aldrich.

Dental Plaque

Plaque is a sticky film, more specifically a biofilm. Biofilms are aggregations of microorganisms that secrete adhesive mucilage, also known as a glycocalyx, thereby gluing themselves to surfaces. While some biofilms are beneficial, dental plaque is a type of harmful biofilm. The acids produced by the bacteria of dental plaque damage tooth enamel and surrounding gums, and can lead to tooth decay, gingivitis, and periodontitis Recent studies suggest that strains of the bacteria *Bacillus licheniformis* found on *A. nodosum* produce extracellular enzymes, such as various proteases and lipases. *B. licheniformis* also release a nuclease which is capable of hydrolyzing the phosphodiester backbone of DNA. It is hypothesized that these enzymes break up the biofilm and release the bacteria, thus helping to break down oral plaque and reducing dental carries.

With the exception of a few catalytic RNA molecules, enzymes are proteins. Enzymes catalyze specific metabolic reactions, either to build new molecules (anabolic reactions), or break them down into simpler products (catabolic reactions). There are many different types and classes of enzymes. For example, hydrolases are a group of approximately 200 enzymes that use water to break bonds within compounds, separating them into simpler products. Included in the hydrolase group are, for example, esterases, which include lipases, phosphatases, which include nucleases, glycosidases, which include carboydrases and amylases, and peptidases (also known as proteinases or proteases). Other classes of enzymes include isomerases, ligases, lyases, oxidoreductases, and transferases.

Enzyme Production from *B. licheniformis*

To prepare the composition of the present disclosure, *B. licheniformis* may be cultured and induced to produce enzymes by any number of means known in the art. *B. licheniformis* is a Gram-positive endospore forming organism that can be isolated from soils and plant material all over the world. Additionally, various strains can be obtained from a number of microbial depositories. This organism is used extensively for large-scale industrial production of exoenzymes as it can secrete large quantities of proteins of up to 20-25 g/l (Divakaran D, Chandran A, Pratap Chandran R. Comparative study on production of α-Amylase from *Bacillus licheniformis* strains. *Brazilian Journal of Microbiology*. 2011; 42(4):1397-1404).

A. Alkaline Proteases

For example, as reported by Sarker et al., to produce alkaline proteases from *B. licheniformis*, a media containing glucose, peptone, $K_2HPO_4$, $MgSO_4$ and $Na_2CO_3$ at pH 10 was used. Maximum level of enzyme production was obtained after 48 h of incubation with 2% inoculum size at 42° C., under continuous agitation at 150 rpm, in growth medium of pH 9. Highest enzyme production was obtained using 1% rice flour as carbon source and 0.8% beef extract as organic nitrogen source. This particular enzyme is suitable for industrial applications such as in the detergent, food, pharmaceutical, and leather industries (see for example, Sarker P K, Talukdar S A, Deb P, Sayem S A, Mohsina K.

Optimization and partial characterization of culture conditions for the production of alkaline protease from *Bacillus licheniformis* P003. *SpringerPlus*. 2013; 2:506). See also U.S. Pat. No. 4,559,307, incorporated herein by reference for all that it discloses and teaches.

B. Alpha Amylase

To produce α-amylase, an extracellular enzyme that breaks down starch into the disaccharide maltose, Divakaran et al., used two strains of *Bacillus licheniformis*, MTCC 2617 and 2618, and four different substrates, starch, rice, wheat and ragi powder, as a carbon source by submerged fermentation. After culture and centrifugation, the supernatant was purified to obtain crude enzyme, which was further purified by ammonium sulfate precipitation, dialysis and ion-exchange chromatography to obtain pure enzyme. Amylase has extensive application in food, starch liquefaction, saccharification, detergent, brewing, paper, textile and distilling industries (see for example, Divakaran D, Chandran A, Pratap Chandran R. Comparative study on production of α-Amylase from *Bacillus licheniformis* strains. *Brazilian Journal of Microbiology*. 2011; 42(4):1397-1404).

C. Keratinase

Lin et al. isolated a keratinase from the culture medium of feather-degrading *Bacillus licheniformis* PWD-1 by use of an assay of the hydrolysis of azokeratin. Membrane ultra-filtration and carboxymethyl cellulose ion-exchange and SEPHADEX G-75 gel chromatographies were used to purify the enzyme (see for example, Xiang Lin, Chung-Ginn Lee, Ellen S. Casale, Jason C. H. Shih, Appl. Environ. Microbiol. October 1992 vol. 58 no. 10 pg 3271-3275). See also U.S. Pat. No. 5,171,682, incorporated herein by reference for all that it discloses and teaches.

E. Mannanase

Zhang et al. reported a technique for purifying ß-mannanase from *B. licheniformis* using flocculation, ultrafiltration, and ion-exchange chromatography. Mannanses are useful in the food and feed processing industries, pulp and paper industries, and the stimulation of oil and gas well (see for example, Zhang, J, He, Z. and Hu K. *Biotechnology Letters*, 2000 vol. 22 pg 1375-1378).

Examples of production and purification of additional enzymes of industrial importance include, but are not limited to, esterase (see for example, European Patent Publication No. 0549264, incorporated herein by reference for all that it discloses and teaches), and phytases (see for example, U.S. Patent Publication No. 20070277257, incorporated herein by reference for all that it discloses and teaches).

Additional enzymes which may be produced by *B. licheniformis* or other organisms, for example yeast and other eukaryotic organisms, and included in the composition of matter of the present disclosure include, but are not limited to, oxidoreductase, transferase, hydrolase, lyase, isomerase, ligase, aminopeptidase, asparaginase, carbohydrase, carboxypeptidase, catalase, cellulose, chitinase, cutinase, cyclodextrin glycosyltransferase, deoxyribonuclease, alpha galactosidase, beta-galactosidase, glucoamylase, alpha-glucosidase, betaglucosidase, hyaluronic acid synthase, invertase, laccase, lipase, mannosidase, mutanase, oxidase, pectinolytic enzymes, peroxidase, polyphenoloxidase, ribonuclease, transglutaminase, and xylanase. See for example, International Publication No. W2016/180928, incorporated herein by reference for all that it discloses and teaches.

The composition may further comprise additives including, but not limited to, sorbitol, dextrin, maltodextrin, collagen, glycerine, hexoses, glucosamine, and mixtures thereof.

The composition may further comprise natural polymers, including but not limited to, starches, for example potato starch, corn starch, wheat starch, tapioca starch, and pea starch, pectins, gum Arabic, acacia gum, guar gum, Xanthan gum, proteins, for example, egg whites, pea protein, and glutein, and oils, for example, coconut oil, canola oil, or corn oil.

The composition may further comprise synthetic polymers, including but not limited to, polypropylene glycol, polyethylene glycol, polyvinyl alcohol, and hydroxypropylmethyl cellulose.

The natural and synthetic polymers listed above facilitate binding the enzymes and/or bacteria to the animal chew and also enable the composition to dissolve, releasing the enzymes and/or bacteria into the animal's mouth.

The composition may further comprise a sugar, an edible toothpaste, a nutraceutical, a water-soluble thickener, or a combination thereof.

Sugars may include, but are not limited to, agave nectar, barley malt syrup, barley sugar birch syrup, brown sugar, caramel, coconut sugar, corn syrup, date sugar, dextrose, sucrose, lactose, maltose, fructose, galactose, glucose, golden syrup, high fructose corn syrup, high maltose corn syrup, honey, confectioners' sugar, inositol, inverted sugar syrup, jiggery, mannose, maple sugar, maple syrup, molasses (from sugar beets), molasses (from sugar cane), palm sugar, ribose, rhamnose, toffee, treacle, trehalose, xylose, and mixtures thereof.

In addition to providing a pleasing taste, the above listed sugars will also help to facilitate solvation of the composition coating the animal chew.

Water soluble thickeners, may include, but are not limited to, gelatin, carboxymethylcellulose, agar, starch, carrageen, and mixtures thereof.

An edible toothpaste, may include, but is not limited to, dental grade silica abrasive, dicalcium phosphate dihydrate, pumice, polyphosphate, microcrystalline cellulose, magnesium stearate, and mixtures thereof.

Nutraceuticals may include, but are not limited to, brewer's yeast, *Echinacea purpurea, Ascophyllum nodosum*, flax seed, polyunsaturated fatty acids, calcium, vitamins and minerals, and combinations thereof.

The composition may further comprise a color additive, a flavoring additive (palatant enhancer), a binder, an emulsifier, a preservative, an antioxidant, or a combination thereof.

The composition may further comprise at least one strain of *Lactobacillus* and an enzyme produced from said *Lactobacillus*.

The composition may further comprise at least one of a hydrolase, isomerase, ligase, lyase, oxidoreductase, and transferase.

The composition may be formulated as an aqueous solution, a non-aqueous solution, a suspension, a gel, a foam, a paste, a powder, a dust, a solid, or an emulsion.

Following culture and/or production and purification of extracellular enzymes of *B. licheniformis*, the isolates may be mixed with natural and/or synthetic compounds or mixtures of compounds.

The above composition may further comprise additional bacteria and/or enzymes. For example, certain strains of *Lactobacillus* have been shown to be effective at reducing the number of *Streptococcus mutans* in the mouth of mammals. Such strains include but are not limited to, *Lactobacillus reuteri, L. salivarus*, and *L. rhamnosus*.

The above composition may further comprise various color and flavoring additives, binders, emulsifiers, preservatives, and antioxidants, and may be formulated as an aqueous solution, a non-aqueous solution, a suspension, a gel, a foam, a paste, a powder, a dust, a solid, or an emulsion.

As used herein, "animal" means organisms that form the biological kingdom Animalia, for example, humans, domesticated animals such as dogs, cats, cattle, horses, pigs, etc. and undomesticated animals such as deer, elk, alpacas, lamas, and moose, carnivores, such as bears, wolves, lions, and tigers, rodents, such as rats, mice, and beaver, bats, marsupials, such as kangaroos and opossums and cetaceans, such as whales, dolphins, and porpoises.

Another embodiment of the present disclosure provides for a method for manufacturing an animal chew or food item comprising coating at least a portion of said animal chew or food item with a composition of matter comprising at least one of a strain of the bacteria Bacillus licheniformis and an extracellular enzyme produced from said B. licheniformis; and at least one of a natural polymer and synthetic polymer.

As used herein, "animal chew" means any material suitable for consumption by an animal. A variety of natural and synthetic animal chews may be used, including but not limited to, bully sticks, Himalayan dog chews, antler chews, rubber chews, rawhides, pig ears, pig skins, nylon chews, real bones, cow hooves, protein chews, and carbohydrate chews, for example, those composed of potato starch, rice flour, tapioca starch, pea flour, or pea starch. The above composition may also be applied to a variety of animal food types and treats for consumption.

The composition may further comprise additives including, but not limited to, sorbitol, dextrin, maltodextrin, collagen, glycerine, hexoses, glucosamine, and mixtures thereof.

The composition may further comprise natural polymers, including but not limited to, starches, for example potato starch, corn starch, wheat starch, tapioca starch, and pea starch, pectins, gum Arabic, acacia gum, guar gum, Xanthan gum, proteins, for example, egg whites, pea protein, and glutein, and oils, for example, coconut oil, canola oil, or corn oil.

The composition may further comprise synthetic polymers, including but not limited to, polypropylene glycol, polyethylene glycol, polyvinyl alcohol, and hydroxypropylmethyl cellulose.

The composition may further comprise a sugar, an edible toothpaste, a nutraceutical, a water-soluble thickener, or a combination thereof.

Sugars may include, but are not limited to, agave nectar, barley malt syrup, barley sugar birch syrup, brown sugar, caramel, coconut sugar, corn syrup, date sugar, dextrose, sucrose, lactose, maltose, fructose, galactose, glucose, golden syrup, high fructose corn syrup, high maltose corn syrup, honey, confectioners' sugar, inositol, inverted sugar syrup, jiggery, mannose, maple sugar, maple syrup, molasses (from sugar beets), molasses (from sugar cane), palm sugar, ribose, rhamnose, toffee, treacle, trehalose, xylose, and mixtures thereof.

Water soluble thickeners, may include, but are not limited to, gelatin, carboxymethylcellulose, agar, starch, carrageen, and mixtures thereof.

An edible toothpaste, may include, but is not limited to, dental grade silica abrasive, dicalcium phosphate dihydrate, pumice, polyphosphate, microcrystalline cellulose, magnesium stearate, and mixtures thereof.

Nutraceuticals may include, but are not limited to, brewer's yeast, *Echinacea purpurea, Ascophyllum nodosum*, flax seed, polyunsaturated fatty acids, calcium, vitamins and minerals, and combinations thereof.

The composition may further comprise a color additive, a flavoring additive (palatant enhancer), a binder, an emulsifier, a preservative, an antioxidant, or a combination thereof.

The composition may further comprise at least one strain of *Lactobacillus* and an enzyme produced from said *Lactobacillus*.

The composition may further comprise at least one of a hydrolase, isomerase, ligase, lyase, oxidoreductase, and transferase.

The composition may be formulated as an aqueous solution, a non-aqueous solution, a suspension, a gel, a foam, a paste, a powder, a dust, a solid, or an emulsion.

Following culture and/or production and purification of extracellular enzymes of *B. licheniformis*, the isolates may be mixed with natural and/or synthetic compounds or mixtures of compounds.

The method may further comprise coating by dipping or spraying said animal chew or food item with said composition. As will be understood by one skilled in the art, any number of means of coating processes and/or equipment may be used, in particular those that avoid excessive heat, wherein at least a portion of the surface of the animal chew is coated with the disclosed composition. For example, the animal chew may be dipped, or sprayed with the composition disclosed herein and allowed to dry The method above, wherein said animal chew or food item is chosen from bully sticks, Himalayan dog chews, antler chews, rubber chews, rawhides, pig ears, pig skins, nylon chews, real bones, cow hooves, and corn starch chews.

Another embodiment provides for an animal chew or food item produced by the methods disclosed herein.

The method may further comprise a second coating on the animal chew product produced above, wherein the second coating comprises collagen, gelatin, glycerin, or combinations thereof.

EXAMPLES

The following examples are provided to illustrate further the various applications and are not intended to limit the invention beyond the limitations set forth in the appended claims.

Example 1—a Method of Coating an Animal Chew with a Composition Comprising Extracellular Enzymes Produced by *B. licheniformis*

*B. licheniformis* is commonly found in, and can be obtained from, the soil, on bird feathers, and most recently on the seaweed *A. nodosum*. *B. licheniformis* can also be obtained from any number of microbial depositories and commercially purchased. As shown in the flow diagram of FIG. 1, *B. licheniformis* is cultured (101) and then induced to produce a desired enzyme (103). A number of culturing techniques for the production of enzymes are well known in the art. See for example, Divakaran D, Chandran A, Pratap Chandran R. Comparative study on production of α-Amylase from *Bacillus licheniformis* strains. *Brazilian Journal of Microbiology*. 2011; 42(4):1397-1404, Sarker P K, Talukdar S A, Deb P, Sayem S A, Mohsina K. Optimization and partial characterization of culture conditions for the production of alkaline protease from *Bacillus licheniformis* P003. *SpringerPlus*. 2013; 2:506, Xiang Lin, Chung-Ginn Lee, Ellen S. Casale, Jason C. H. Shih, Appl. Environ. Microbiol. October 1992 vol. 58 no. 10 pg 3271-3275, and Zhang, J, He, Z. and Hu K. *Biotechnology Letters*. 2000 vol. 22 pg 1375-1378.

Following culture and enzyme production, the enzymes are extracted and purified (105). A number of enzyme extraction and purification methods are well known in the art. See for example, Divakaran D, Chandran A, Pratap Chandran R. Comparative study on production of α-Amylase from *Bacillus licheniformis* strains. *Brazilian Journal of Microbiology*. 2011; 42(4):1397-1404, Sarker P K, Talukdar S A, Deb P, Sayem S A, Mohsina K. Optimization and partial characterization of culture conditions for the production of alkaline protease from *Bacillus licheniformis* P003. *SpringerPlus*. 2013; 2:506, Xiang Lin, Chung-Ginn Lee, Ellen S. Casale, Jason C. H. Shih, Appl. Environ. Microbiol. October 1992 vol. 58 no. 10 pg 3271-3275, and Zhang, J, He, Z. and Hu K. *Biotechnology Letters*, 2000 vol. 22 pg 1375-1378. See also U.S. Pat. Nos. 4,559,307, 5,171,682, U.S. Patent Publication No. 20070277257, and International Publication No. WO2016/180928, incorporated herein by reference for all they disclose and teach.

The purified enzymes are then mixed with natural and/or synthetic polymers, additional compounds, and/or enzymes (107). Examples of additional compounds may include for example, sorbitol, polyethylene glycol, dextrin, maltodextrin, collagen, glycerine, oil or fat, mineral oil, glucose, glucose oxidase, hexose, myeloperoxidase, potassium thiocyanate, lactoperoxidase, potassium thiocyanate, glucosamine, and mixtures thereof, thickeners, edible toothpastes, nutraceuticals, certain strains of *Lactobacillus*, various color and flavoring additives, binders, emulsifiers, preservatives, and antioxidants, and may be formulated as a liquid or a powder.

The composition is then applied to the surface of an animal chew or food item (109) using minimal heat during processing and drying. Examples of animal chews or food items include, for example, bully sticks, Himalayan dog chews, antler chews, rubber chews, rawhides, pig ears, pig skins, nylon chews, real bones, cow hooves, protein chews, and carbohydrate chews, for example, those composed of potato starch, rice flour, tapioca starch, pea flour, or pea starch.

The coating dissolves quickly in the animal's mouth, releasing the enzymes and/or bacteria.

Example 2—Recipe for Composition Comprising Extracellular Enzymes Produced by *B. licheniformis*

The following is an example recipe for the composition disclosed herein.

TABLE 1

| Ingredient | Amount |
| --- | --- |
| Egg Whites | Approximately 50% |
| Dextrose | Approximately 49.999% |
| Enzymes or Bacteria | Approximately 0.001% |

As shown above in Table 1, the composition of the present disclosure may comprise approximately 50% egg whites, approximately 49.999% dextrose, and approximately 0.001% enzymes or bacteria.

Example 3—Recipe for Composition Comprising Extracellular Enzymes Produced by *B. licheniformis*

The following is an example recipe for the composition disclosed herein.

TABLE 2

| Ingredient | Amount |
| --- | --- |
| Egg Whites | Between 20% and 40% |
| Sugar | Between 30% and 50% |
| Palatant Enhancer | Between 1% and 5% |
| Gelatin | Between 1% and 5% |
| Enzymes or Bacteria | Less than or equal to 0.005% |

As shown above in Table 2, the composition of the present disclosure may comprise between 20% and 40% egg whites, between 30% and 50% sugar, between 1% and 5% Palatant Enhancer, between 1% and 5% gelatin, and less than or equal to 0.005% enzymes or bacteria.

Example 4—Recipe for Composition Comprising Extracellular Enzymes Produced by *B. licheniformis*

The following is an example recipe for the composition disclosed herein.

TABLE 3

| Ingredient | Amount |
| --- | --- |
| Dextrin | Between 5% and 20% |
| Maltodextrin | Between 20% and 50% |
| Glucose | Between 10% and 40% |
| Palatant Enhancer | Between 1% and 5% |
| Starch | Between 1% and 3% |
| Oil or Fat | Between 1% and 3% |
| Enzymes or Bacteria | Less than or equal to 0.005% |

As shown above in Table 3, the composition of the present disclosure may comprise between 5% and 20% dextrin, between 20% and 50% maltodextrin, between 10% and 40% glucose, between 1% and 5% Palatant Enhancer, between 1% and 3% starch, between 1% and 3% oil or fat, and less than or equal to 0.005% enzymes or bacteria.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

The invention claimed is:

1. A method of manufacturing an animal chew that removes dental plaque, said method comprising:

applying a first coating on at least a portion of a surface of the animal chew by dipping or spraying said portion with a composition that removes dental plaque, wherein the composition comprises a strain of *Bacillus licheniformis* obtained from Norwegian kelp, an extracellular enzyme produced by said *Bacillus licheniformis*, and at least one of a natural polymer and a synthetic polymer, and allowing said first coating to dry; and applying a second coating on said portion of the surface of the animal chew, wherein the said second coating comprises collagen, gelatin, glycerin, or a combination thereof.

2. The method of claim 1, wherein said composition further comprises a color additive, a flavoring additive, a binder, an emulsifier, a preservative, an antioxidant, or a combination thereof.

3. The method of claim 1, wherein said composition is formulated as an aqueous solution, a non-aqueous solution, a suspension, a gel, a foam, a paste, a powder, a dust, a solid, or an emulsion.

4. The method of claim 1, wherein said animal chew is chosen from bully sticks, Himalayan dog chews, antler chews, rubber chews, rawhides, pig ears, pig skins, nylon chews, real bones, cow hooves, and corn starch chews.

* * * * *